US00PP24234P2

(12) United States Plant Patent
Misato

(10) Patent No.: US PP24,234 P2
(45) Date of Patent: Feb. 11, 2014

(54) ***VERBENA* PLANT NAMED 'SUNMARICOHO'**

(50) Latin Name: *Verbena hybrida*
Varietal Denomination: Sunmaricoho

(75) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 131 days.

(21) Appl. No.: 13/385,289

(22) Filed: Feb. 10, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — June Hwu
(74) *Attorney, Agent, or Firm* — C. A. Whealy

(57) ABSTRACT

A new and distinct cultivar of *Verbena* plant named 'Sunmaricoho', characterized by its compact, upright and mounding plant habit; moderately vigorous to vigorous growth habit; freely branching habit; early and freely flowering habit; long flowering period; white-colored flowers that are held above and beyond the foliar plane; and good garden performance.

1 Drawing Sheet

Botanical designation: *Verbena hybrida.*
Cultivar denomination: 'SUNMARICOHO'.

BACKGROUND OF THE INVENTION

The present invention relates to a new and distinct cultivar of *Verbena* plant, botanically known as *Verbena hybrida*, and hereinafter referred to by the name 'Sunmaricoho'.

The new *Verbena* plant is a product of a planned breeding program conducted by the Inventor in Higashiomi, Shiga, Japan. The objective of the breeding program is to create new compact, upright and mounding *Verbena* plants that are freely-branching and have white-colored flowers.

The new *Verbena* plant originated from a cross-pollination made by the Inventor in September, 2006 in Higashiomi, Shiga, Japan of a proprietary selection of *Verbena hybrida* identified as code number VW416, not patented, as the female, or seed, parent with a proprietary selection of *Verbena hybrida* identified as code number 02H-11-2, not patented, as the male, or pollen, parent. The new *Verbena* plant was discovered and selected by the Inventor as a single flowering plant within the progeny of the stated cross-pollination in a controlled greenhouse environment in Higashiomi, Shiga, Japan in October, 2007.

Asexual reproduction of the new *Verbena* plant by terminal cuttings in a controlled environment in Higashiomi, Shiga, Japan since October, 2007 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunmaricoho'. These characteristics in combination distinguish 'Sunmaricoho' as a new and distinct *Verbena* plant:

1. Compact, upright and mounding plant habit.
2. Moderately vigorous to vigorous growth habit.
3. Freely branching habit.
4. Early and freely flowering habit.
5. Long flowering period.
6. White-colored flowers that are held above and beyond the foliar plane.
7. Good garden performance.

Plants of the new *Verbena* can be compared to plants of the female parent selection. Plants of the new *Verbena* differ primarily from plants of the female parent selection in the following characteristics:

1. Plants of the new *Verbena* are more upright than and not as trailing as plants of the female parent selection.
2. Plants of the new *Verbena* are more freely branching than plants of the female parent selection.

Plants of the new *Verbena* can be compared to plants of the male parent selection. Plants of the new *Verbena* differ primarily from plants of the male parent selection in the following characteristics:

1. Plants of the new *Verbena* are more upright than and not as trailing as plants of the male parent selection.
2. Plants of the new *Verbena* and the male parent selection differ in flower color as plants of the male parent selection have cream-colored flowers.

Plants of the new *Verbena* can be compared to plants of *Verbena* 'Sunmarivani', disclosed in U.S. Plant Pat. No. 17,594. In side-by-side comparisons conducted in Higashiomi, Shiga, Japan, plants of the new *Verbena* differed primarily from plants of 'Sunmarivani' in the following characteristics:

1. Plants of the new *Verbena* were more upright than and not as trailing as plants of 'Sunmarivani'.
2. Plants of the new *Verbena* were taller than and not as broad as plants of 'Sunmarivani'.
3. Plants of the new *Verbena* had slightly smaller leaves than plants of 'Sunmarivani'.
4. Plants of the new *Verbena* were more freely flowering than plants of 'Sunmarivani'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena*.

The photograph at the top of the sheet comprises a side perspective view of a typical flowering plant of 'Sunmaricoho' grown in a container.

The photograph at the bottom of the sheet is a close-up view of a typical inflorescence of 'Sunmaricoho'.

DETAILED BOTANICAL DESCRIPTION

The aforementioned photographs and following observations and measurements describe plants grown during the late spring and early summer in 15-cm containers in an outdoor nursery in Higashiomi, Shiga, Japan under commercial practices typical of commercial *Verbena* production. During the production of the plants, day temperatures averaged 23° C. and night temperatures averaged 13° C. Plants were four months old when the photographs and description were taken. In the following description color references are made to The Royal Horticultural Society Colour Chart, 2007 Edition, except where general terms of ordinary dictionary significance are used.

Botanical classification: *Verbena hybrida* 'Sunmaricoho'.

Parentage:

*Female, or seed, parent.*—Proprietary selection of *Verbena hybrida* identified as code number VW416, not patented.

*Male, or pollen, parent.*—Proprietary seedling selection of *Verbena hybrida* identified as code number 02H-11-2, not patented.

Propagation:

*Type.*—By terminal cuttings.

*Time to initiate roots.*—About 10 to 14 days at 20° C. to 25° C.

*Time to produce a rooted young plant.*—About four weeks at 20° C. to 25° C.

*Root description.*—Fibrous; white in color.

*Rooting habit.*—Freely branching.

Plant description:

*Plant and growth habit.*—Compact, upright and mounding growth habit; freely branching habit with numerous lateral branches developing per plant; pinching enhances lateral branch development; moderately vigorous to vigorous growth habit.

*Plant height.*—About 22.8 cm.

*Plant diameter.*—About 39.8 cm.

Lateral branch description:

*Length.*—About 16.8 cm.

*Diameter.*—About 2 mm.

*Internode length.*—About 3.3 cm.

*Strength.*—Strong.

*Aspect.*—Upright to semi-upright.

*Texture.*—Densely pubescent.

*Color.*—Close to 143C.

Foliage description:

*Arrangement.*—Opposite, simple.

*Length.*—About 3.7 cm.

*Width.*—About 2.3 cm.

*Shape.*—Ovate.

*Apex.*—Broadly acute.

*Base.*—Cuneate.

*Margin.*—Serrate.

*Texture, upper and lower surfaces.*—Densely pubescent.

*Venation pattern.*—Pinnate; reticulate.

*Color.*—Developing leaves, upper surface: Close to 143C. Developing leaves, lower surface: Close to 143D. Fully expanded leaves, upper surface: Close to 137C; venation, close to 145C. Fully expanded leaves, lower surface: Close to 138B; venation, close to 145C.

*Petiole.*—Length: About 5.1 cm. Diameter: About 1.6 mm. Texture, upper and lower surfaces: Pubescent. Color, upper and lower surfaces: Close to 145C.

Flower description:

*Flower arrangement and flowering habit.*—Single salverform flowers arranged in hemispherical terminal racemes; flowers face mostly upright; freely flowering habit with about 23 flowers per inflorescence and about 27 inflorescences developing per plant.

*Natural flowering season.*—Early flowering habit, plants begin flowering about four weeks after planting; long flowering period, plants flower continuously from spring to late autumn in Japan.

*Flower longevity.*—Flowers last about one week on the plant; flowers not persistent.

*Fragrance.*—Fragrant, pleasant.

*Inflorescence height.*—About 3.8 cm.

*Inflorescence diameter.*—About 5.9 cm.

*Flowers.*—Appearance: Flared trumpet, corolla fused, five-parted. Diameter: About 2 cm. Depth (height): About 2.4 cm. Tube length: About 2.1 cm. Tube diameter, mid-section: About 1.3 mm.

*Flower buds.*—Length: About 1.5 cm. Diameter: About 2.6 mm. Shape: Clavate. Color: Close to NN155A.

*Corolla.*—Arrangement: Single whorl of five fused petals. Petal length: About 8.8 mm. Petal width: About 8 mm. Petal lobe shape: Cordate. Petal lobe apex: Emarginate. Petal margin: Entire. Petal texture, upper and lower surfaces: Smooth, glabrous. Tube texture: Smooth, glabrous. Color: Petal, when opening, upper and lower surfaces: Close to NN155D. Petal, fully opened, upper and lower surfaces: Close to NN155D. Throat: Close to 145D. Tube: Close to 145D.

*Calyx.*—Arrangement: One single narrow calyx tube per flower with five fused sepals. Sepal length: About 1 mm. Sepal width: About 0.8 mm. Sepal shape: Deltoid. Sepal apex: Acute. Sepal margin: Entire. Sepal texture, upper and lower surfaces: Smooth, glabrous. Sepal color, upper and lower surfaces: Close to 144A to 144D.

*Peduncles.*—Length: About 6.8 cm. Diameter: About 1.2 mm. Strength: Strong. Texture: Pubescent. Color: Close to 143C.

*Reproductive organs.*—Stamens: Quantity and arrangement: Four per flower, adnate to corolla tube. Anther shape: Ellipsoidal. Anther length: About 0.8 mm. Anther color: Close to 143C and 144C. Pollen amount: None observed. Pistils: Quantity: One per flower. Pistil length: About 1.8 cm. Stigma shape: Bi-parted. Stigma color: Close to 144B. Style color: Close to 144C. Ovary color: Close to 144C. Fruits and seeds: Fruit and seed development have not been observed on plants of the new *Verbena*.

Garden performance: Plants of the new *Verbena* have been observed to have good garden performance and to tolerate wind, rain and temperatures ranging from about 0° C. to about 35° C.

Pathogen/pest resistance: Plants of the new *Verbena* have not been observed to be resistant to pathogens and pests common to *Verbena* plants.

It is claimed:

1. A new and distinct *Verbena* plant named 'Sunmaricoho' as illustrated and described.

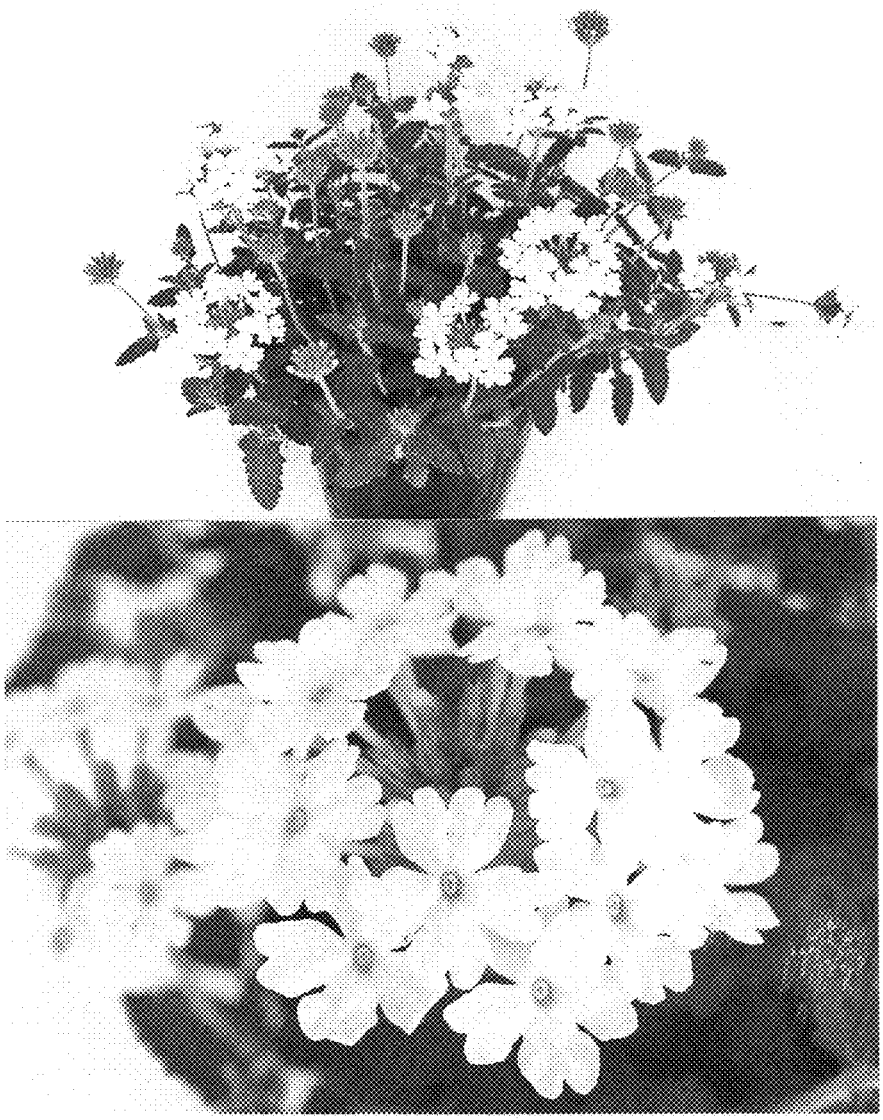

* * * * *